US011754534B2

(12) United States Patent
Kim et al.

(10) Patent No.: US 11,754,534 B2
(45) Date of Patent: Sep. 12, 2023

(54) ULTRASONIC PROBE AND METHOD OF MANUFACTURING THE SAME

(71) Applicant: SAMSUNG MEDISON CO., LTD., Gangwon-do (KR)

(72) Inventors: Jisu Kim, Seoul (KR); Kwangjin Son, Seoul (KR); Jong-Sun Ko, Seoul (KR); Joonghyun Park, Seoul (KR); Jinwoo Jung, Seoul (KR); Youngmon Cho, Seoul (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 172 days.

(21) Appl. No.: 17/167,575

(22) Filed: Feb. 4, 2021

(65) Prior Publication Data

US 2021/0255149 A1    Aug. 19, 2021

(30) Foreign Application Priority Data

Feb. 18, 2020   (KR) .................. 10-2020-0019463

(51) Int. Cl.
  *G01N 29/24* (2006.01)
  *B06B 1/06* (2006.01)
  *H10N 30/088* (2023.01)

(52) U.S. Cl.
  CPC ......... *G01N 29/2437* (2013.01); *B06B 1/067* (2013.01); *H10N 30/088* (2023.02)

(58) Field of Classification Search
  CPC .. G01N 29/2437; B06B 1/067; B06B 1/0607; B06B 2201/76; H01L 41/338; A61B 8/4281; A61B 8/4483; A61B 8/4444; A61B 8/4488; A61B 8/4494; A61B 8/5207; A61B 2562/12; G10K 11/02; Y10T 29/42
  See application file for complete search history.

(56) References Cited

U.S. PATENT DOCUMENTS 8,562,534 B2   10/2013   Saito
9,056,333 B2    6/2015   Osawa
(Continued)

FOREIGN PATENT DOCUMENTS

EP   2014236 A1   1/2009
EP   2614897 A2   7/2013
(Continued)

OTHER PUBLICATIONS

Extended Search Report issued by the European Patent Office corresponding to European Application No. 21155301.1, dated Jun. 25, 2021.

*Primary Examiner* — Tarun Sinha
(74) *Attorney, Agent, or Firm* — Morgan, Lewis & Bockius LLP

(57) ABSTRACT

Disclosed are an ultrasonic probe and a method of manufacturing the same. The ultrasonic probe includes a piezoelectric layer including one or more kerfs such that piezoelectric elements are provided in a plurality of rows along an elevation direction, a first electrode formed on an upper side of the piezoelectric layer, a second electrode formed on a lower side of the piezoelectric layer, a matching layer disposed above the piezoelectric layer and including one or more grooves connected to the one or more kerfs, and a third electrode formed in inner surfaces of the one or more grooves and electrically connected to the first electrode.

18 Claims, 11 Drawing Sheets

(56) References Cited

U.S. PATENT DOCUMENTS

| | | | |
|---|---|---|---|
| 2007/0261493 A1* | 11/2007 | Kim | G01M 5/0033 73/594 |
| 2009/0069691 A1* | 3/2009 | Saito | G10K 11/02 600/459 |
| 2013/0181577 A1* | 7/2013 | Min | H01L 41/22 29/25.35 |
| 2013/0293066 A1 | 11/2013 | Tsuzuki et al. | |
| 2018/0040805 A1* | 2/2018 | Motoki | H01L 41/113 |

FOREIGN PATENT DOCUMENTS

| | | |
|---|---|---|
| EP | 3264795 A1 | 1/2018 |
| JP | 61-253999 A | 11/1986 |
| JP | 2012-257017 A | 12/2012 |
| KR | 10-1137262 B1 | 4/2012 |
| KR | 10-1145152 B1 | 5/2012 |
| KR | 10-2016-0088721 A | 7/2016 |

\* cited by examiner

ULTRASONIC PROBE AND METHOD OF MANUFACTURING THE SAME

CROSS-REFERENCE TO RELATED APPLICATION(S)

This application is based on and claims priority under 35 U.S.C. § 119 to Korean Patent Application No. 10-2020-0019463, filed on Feb. 18, 2020, in the Korean Intellectual Property Office, the disclosure of which is incorporated by reference herein in its entirety.

BACKGROUND

1. Field

The disclosure relates to a multi-row ultrasonic probe having an improved structure and a method of manufacturing the same.

2. Description of the Related Art

An ultrasonic imaging apparatus is an apparatus that irradiates an ultrasonic signal from a body surface of a target toward a target site in the body and obtains an image of a monolayer or blood flow of soft tissue without invasion by using information of a reflected ultrasonic signal (ultrasonic echo signal).

The ultrasonic imaging apparatus has been widely used for diagnosis of the heart, abdomen, urinary system and obstetrics because it is small, inexpensive, real-time displayable, easy to use, and has a high level of safety because there is no radiation exposure, compared to other imaging apparatuses such as an X-ray diagnostic apparatus, an X-ray CT scanner (Computerized Tomography Scanner), an MRI (Magnetic Resonance Image) and a nuclear medicine diagnostic apparatus.

The ultrasonic imaging apparatus includes an ultrasonic probe for transmitting an ultrasonic signal to a target object to obtain an ultrasonic image of the target object and receiving an ultrasonic echo signal reflected from the target object, and a main body for generating an image of the inside of the target object by using the ultrasonic echo signal received from the ultrasonic probe.

In general, a piezoelectric layer including a piezoelectric material has a ground electrode and a signal electrode, and in order to be electrically connected to the ground electrode, a conductive matching layer or a separate ground electrode is used.

However, the conductive matching layer is susceptible to external impact and may increase the production cost of a probe, and when a separate ground electrode is used, it may be difficult to accurately transmit a signal at high frequencies due to the thickness of the ground electrode.

SUMMARY

It is an aspect of the disclosure to provide an ultrasonic probe capable of securing an electrical connection inside a probe using a non-conductive matching layer and a method of manufacturing the same.

It is another aspect of the disclosure to provide an ultrasonic probe with an improved structure to be applicable even to a structure including a multi-row and a method of manufacturing the same.

Additional aspects of the disclosure will be set forth in part in the description which follows and, in part, will be obvious from the description, or may be learned by practice of the disclosure.

In accordance with an aspect of the disclosure, an ultrasonic probe includes a piezoelectric layer including one or more kerfs such that piezoelectric elements are provided in a plurality of rows along an elevation direction, a first electrode formed on an upper side of the piezoelectric layer, a second electrode formed on a lower side of the piezoelectric layer, a matching layer disposed above the piezoelectric layer and including one or more grooves connected to the one or more kerfs, and a third electrode formed in inner surfaces of the one or more grooves and electrically connected to the first electrode.

A width of the groove may be formed larger than or equal to a width of the kerf.

The third electrode may be formed by a sputtering method.

The ultrasonic probe may further include a fourth electrode formed on one surface of the matching layer provided on a side where the matching layer and the piezoelectric layer are in contact with each other to be electrically connected to the first electrode.

The third electrode and the fourth electrode may be electrically connected to each other.

The third electrode and the fourth electrode may be formed at the same time by a sputtering method.

The ultrasonic probe may further include a circuit layer disposed below the piezoelectric layer.

The circuit layer may be made of a flexible printed circuit board (FPCB) to be electrically connected to the second electrode.

The kerfs formed on the piezoelectric layer may be continuously formed on a reflective layer.

The kerf may be formed on the reflective layer at the same position as the piezoelectric layer.

A depth of the one or more grooves may be formed smaller than a thickness of the matching layer.

The matching layer may be a first matching layer, and the ultrasonic probe may further include a second matching layer disposed above the first matching layer.

A depth of the one or more grooves may be formed larger than a thickness of the first matching layer and smaller than the combined thickness of the first matching layer and the second matching layer.

The first electrode may be a ground electrode and the second electrode may be a signal electrode.

The matching layer may be made of a non-conductive material.

In accordance with another aspect of the disclosure, an ultrasonic probe includes a piezoelectric layer including one or more kerfs such that piezoelectric elements are provided in a plurality of rows along an elevation direction, a first electrode formed on an upper side of the piezoelectric layer, a second electrode formed on a lower side of the piezoelectric layer, a matching layer disposed above the piezoelectric layer and including one or more grooves connected to the one or more kerfs, and a third electrode made of a conductive material filled in the one or more grooves and electrically connected to the first electrode.

A width of the groove may be formed larger than or equal to a width of the kerf.

The ultrasonic probe may further include a fourth electrode formed on one surface of the matching layer provided on a side where the matching layer and the piezoelectric layer are in contact with each other to be electrically connected to the first electrode, wherein the fourth electrode may be electrically connected to the third electrode.

In accordance with another aspect of the disclosure, a method of manufacturing an ultrasonic probe includes forming one or more grooves on a matching layer along an elevation direction, forming electrodes in inner surfaces of the one or more grooves and in a lower surface of the matching layer, adhering the piezoelectric layer to the lower surface of the matching layer, and forming one or more kerfs in the piezoelectric layer with widths smaller than or equal to widths of the one or more grooves to correspond to positions of the one or more grooves so that the piezoelectric layer is divided into a plurality of rows along the elevation direction.

The electrode formed on the matching layer may be electrically connected to a ground electrode of the piezoelectric layer.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Configurations shown in the embodiments and the drawings described in the present specification are only the preferred embodiments of the present disclosure, and thus it is to be understood that various modified examples, which may replace the embodiments and the drawings described in the present specification, are possible when filing the present application.

Like reference numbers or signs in the various figures of the application represent parts or components that perform substantially the same functions.

The terms used herein are for the purpose of describing the embodiments and are not intended to restrict and/or to limit the disclosure. For example, the singular expressions herein may include plural expressions, unless the context clearly dictates otherwise.

The terms "comprises" and "has" are intended to indicate that there are features, numbers, steps, operations, elements, parts, or combinations thereof described in the specification, and do not exclude the presence or addition of one or more other features, numbers, steps, operations, elements, parts, or combinations thereof.

It will be understood that although the terms first, second, etc. may be used herein to describe various components, these components should not be limited by these terms, and the terms are only used to distinguish one component from another.

For example, without departing from the scope of the disclosure, the first component may be referred to as a second component, and similarly, the second component may also be referred to as a first component. The term "and/or" includes any combination of a plurality of related items or any one of a plurality of related items.

The terms "front," "rear," "upper portion," "lower portion," "upper end" and "lower end" used in the following description are defined with reference to the drawings, and the shape and position of each component are not limited by these terms.

Hereinafter, embodiments of the disclosure will be described in detail with reference to the accompanying drawings.

Figure 1:
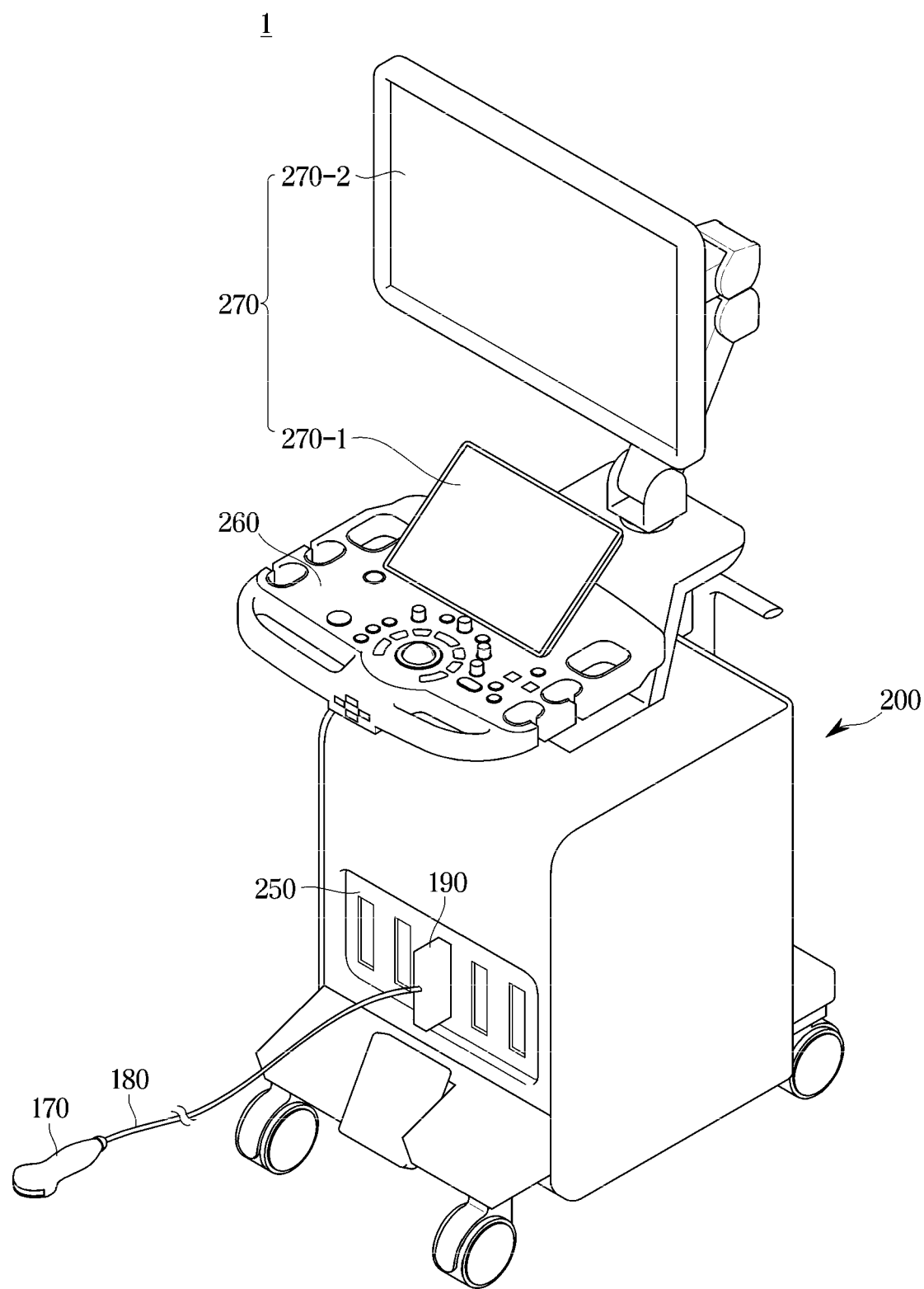
FIG. 1 is a perspective view of an ultrasonic imaging apparatus including an ultrasonic probe according to an embodiment of the disclosure.

FIG. 1 is a perspective view of an ultrasonic imaging apparatus including an ultrasonic probe according to an embodiment of the disclosure.

Referring to FIG. 1, an ultrasonic imaging apparatus includes an ultrasonic probe 100 configured to transmit an ultrasonic signal to an object and receive an echo ultrasonic signal from the object to convert the echo ultrasonic signal into an electrical signal, and a main body 200 configured to generate an ultrasonic image based on an ultrasonic signal.

The main body 200 may be connected to the ultrasonic probe 100 through a wired communication network or a wireless communication network. The main body 200 may be a workstation including a display 270 and an input device 250.

The ultrasonic probe 100 may include a transducer module provided in a housing 170 to irradiate an ultrasonic wave onto an object, receive an echo ultrasonic wave reflected from the object, and convert an electrical signal and an ultrasonic wave to each other.

The main body 200 may include a female connector 250 and a male connector 190.

The male connector 190 is physically coupled to the female connector 250 to transmit and receive signals to and from the main body 200. The main body 200 may also include a cable 180 to connect the male connector 190 and the housing 170 of the ultrasonic probe 100.

An object may be a human or animal living body or tissues in vivo such as blood vessels, bones, muscles, and the like, but is not limited thereto, and as long as its internal structure may be imaged by the ultrasonic imaging apparatus 1, it may be an object.

The ultrasonic probe 100 may be connected to the main body 200 through a wireless communication network to receive various signals required for control of the ultrasonic probe 100. The ultrasonic probe 100 may also transmit an analog signal or a digital signal corresponding to an echo ultrasonic signal received by the ultrasonic probe 100 to the main body 200. The wireless communication network refers to a communication network that may send and receive signals wirelessly.

Echo ultrasonic waves are ultrasonic waves reflected from objects to which the ultrasonic waves are irradiated and have various frequency bands or energy intensities for generating various ultrasonic images depending on diagnosis modes.

The transducer module inside the ultrasonic probe 100 may generate ultrasonic waves according to an applied AC power. The transducer module may generate ultrasonic waves by receiving AC power from an external power supply device or an internal power storage device, such as a battery, and vibrating according to the AC power.

Three directions that are perpendicular to each other with respect to the center of the ultrasonic probe 100 may be defined as an axis direction A, a lateral direction L, and an elevation direction E. Specifically, a direction in which ultrasonic waves are irradiated may be defined as the axial direction A, a direction in which the ultrasonic probe 100 forms horizontal rows may be defined as the lateral direction L, and the remaining direction perpendicular to the axial direction A and the lateral direction L may be defined as the elevation direction E. The ultrasonic probe 100 may also form a plurality of rows in the elevation direction E, and in this case, may form a multi-row array arrangement.

One end of the cable 180 is connected to the housing 170 of the ultrasonic probe 100 and the other end of the cable 180 is connected to the male connector 190, thereby connecting both.

The male connector 190 transmits an electrical signal generated by the transducer module inside the ultrasonic probe 100 to the physically coupled female connector 250, or receives a control signal generated by the main body 200 from the female connector 250.

However, when the ultrasonic probe 100 is implemented as the wireless ultrasonic probe 100, the cable 180 and the male connector 190 may be omitted, and the ultrasonic probe 100 and the main body 200 may transmit and receive signals through a separate wireless communication module (not shown) included in the ultrasonic probe 100. Therefore, the disclosure is not necessarily limited to the shape of the ultrasonic probe 100 illustrated in FIG. 1.

The main body 200 may perform wireless communication with the ultrasonic probe 100 through at least one of a short-range communication module and a mobile communication module.

The display 270 may include an auxiliary display 270-1 and a main display 270-2. When the display 270 is implemented as a touch screen type, the display 270 may also perform the function of an input. That is, the main body 200 may receive various commands from a user through at least one of the display 270 and the input.

In addition, although not shown in the drawings, a voice recognition sensor may be provided in the main body 200 to receive a voice command from a user. Hereinafter, the configuration of the ultrasonic probe 100 will be described in more detail.

Figure 2:
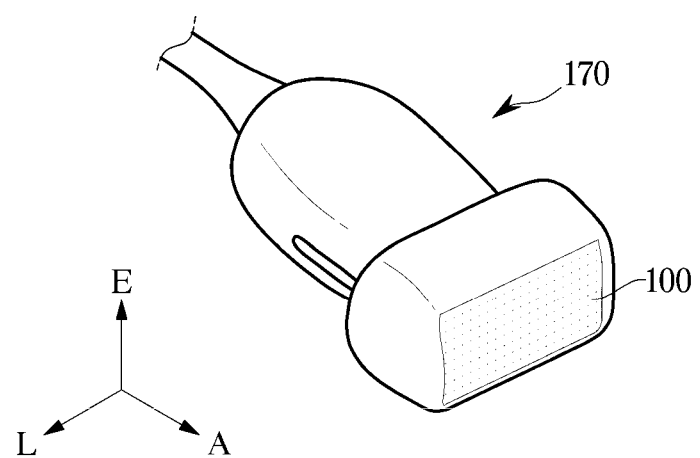
FIG. 2 is an external perspective view of the ultrasonic probe according to an embodiment of the disclosure.

FIG. 2 is an external perspective view of the ultrasonic probe according to an embodiment of the disclosure.

Referring to FIG. 2, the ultrasonic probe 100 may transmit and receive ultrasonic signals as a part that comes in contact with the surface of an object. Specifically, the ultrasonic probe 100 may serve to transmit an ultrasonic signal to a specific portion inside the object according to a transmission signal received from the main body 200 and receive an echo ultrasonic signal reflected from the specific portion inside the object and transmit the echo ultrasonic signal to the main body 200. The echo ultrasonic signal may be an ultrasonic signal that is a radio frequency (RF) signal reflected from the object, but is not limited thereto, and may include all signals in which the ultrasonic signal transmitted to the object is reflected.

The ultrasonic probe 100 may include a transducer array to convert electrical signals and ultrasonic signals to each other in order to transmit ultrasonic signals to the inside of an object. The transducer array may be composed of a single transducer element or multiple transducer elements.

The ultrasonic probe 100 may generate an ultrasonic signal through the transducer array to transmit the ultrasonic signal to a target portion inside an object as a focus and may receive an echo ultrasonic signal reflected from the target portion inside the object through the transducer array.

When the echo ultrasonic signal reaches the transducer array, the transducer array may vibrate at a predetermined frequency corresponding to a frequency of the echo ultrasonic signal to output an AC current having a frequency corresponding to the vibration frequency of the transducer array. Accordingly, the transducer array may convert the received echo ultrasonic signal into an echo signal, which is a predetermined electrical signal.

Each of the transducer elements constituting the transducer array may convert an ultrasonic signal and an electrical signal to each other. To this end, the transducer elements may be implemented as a magnetostrictive ultrasonic transducer using the magnetostrictive effect of a magnetic body, a piezoelectric ultrasonic transducer or a piezoelectric micromachined ultrasonic transducer (pMUT) using the piezoelectric effect of a material, and the like, and may also be implemented as a capacitive micromachined ultrasonic transducer (hereinafter abbreviated as cMUT) that transmits and receives ultrasonic waves using vibrations of hundreds or thousands of finely processed thin films.

The transducer module of the ultrasonic probe 100 may be arranged linearly or in a curved surface as illustrated in FIG. 2. Although the basic operating principles of the ultrasonic probe 100 in both cases are the same, in the ultrasonic probe 100 in which the transducer module is arranged in a curved surface, an ultrasonic signal irradiated to the transducer module has a fan shape, so that the generated ultrasonic image may also have a fan shape.

The transducer module may be provided as a matrix probe. In this case, the transducer module may include a multi-row type multi-dimensional transducer array having a plurality of rows.

Figure 3:
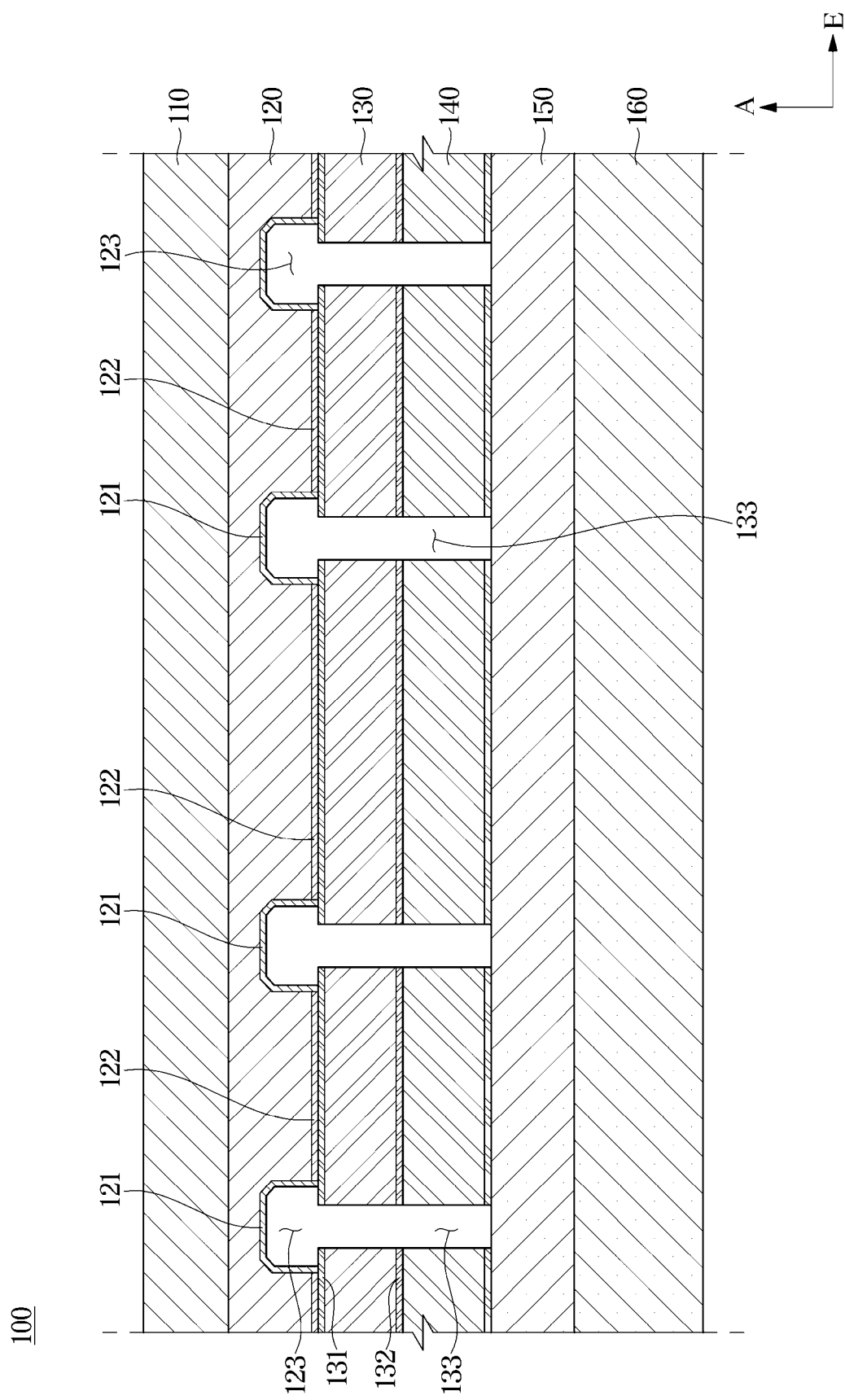
FIG. 3 is a cross-sectional view taken along an axis direction and an elevation direction of the ultrasonic probe according to an embodiment of the disclosure.
Figure 4:
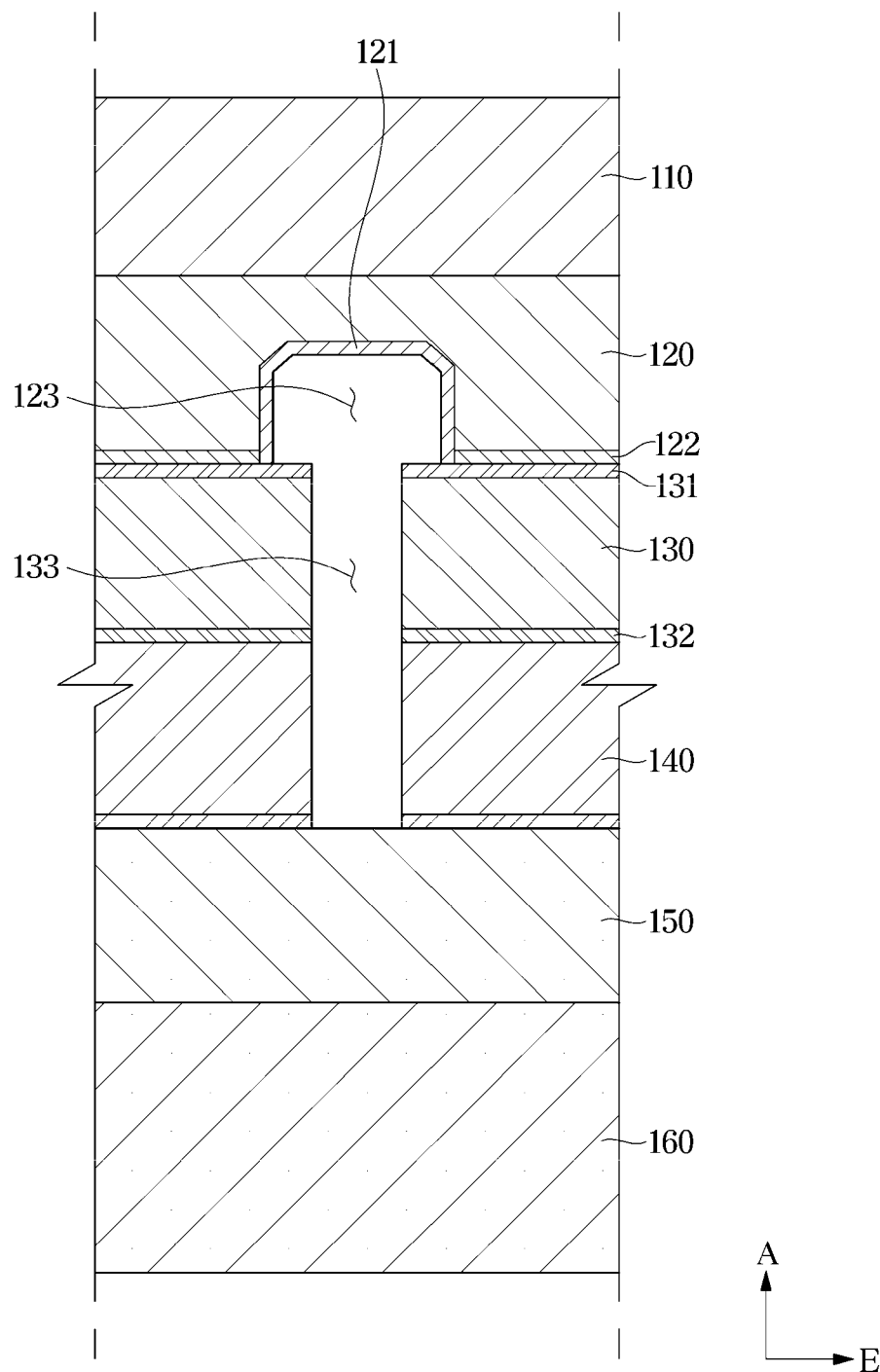
FIG. 4 is an enlarged view of a partial area in FIG. 3.

FIG. 3 is a cross-sectional view taken along an axis direction and an elevation direction of the ultrasonic probe according to an embodiment of the disclosure, and FIG. 4 is an enlarged view of a partial area in FIG. 3.

Referring to FIGS. 3 and 4, the ultrasonic probe 100 includes a piezoelectric layer 130, a sound absorbing layer 160 provided below the piezoelectric layer 130, and matching layers 110 and 120 provided above the piezoelectric layer 130.

The piezoelectric layer 130 is made of a piezoelectric body (piezoelectric material) that converts an electrical signal into mechanical vibration when the electrical signal is applied to generate ultrasonic waves. The piezoelectric body may be laminated in a single layer or multilayer structure.

Effects of generating a voltage when a mechanical pressure is applied to a predetermined material and causing a mechanical deformation when a voltage is applied are referred to as a piezoelectric effect and an inverse piezoelectric effect, respectively.

That is, the piezoelectric body (piezoelectric material) may include a ceramic of lead zirconate titanate (PZT), a PZNT single crystal made of a solid solution of lead magnesium niobate and lead titanate, and the like. The piezoelectric layer 130 may also irradiate mechanical vibration energy as ultrasonic waves in a direction in which a lens is provided and a direction in which the sound absorbing layer 160 is provided. Hereinafter the direction in which the lens is provided is referred to as the front and the direction in which the sound absorbing layer 160 is provided is referred to as the rear, based on the piezoelectric layer 130.

The piezoelectric layer 130 may be processed in the form of a multidimensional array of the form of a matrix forming a plurality of rows by a dicing process.

The sound absorbing layer 160 (backing layer) is disposed below the piezoelectric layer 130 and absorbs ultrasonic waves that are generated in the piezoelectric layer 130 and proceed backward, thereby blocking the ultrasonic waves from proceeding to the rear of the piezoelectric layer 130. Therefore, images may be prevented from being distorted.

The sound absorbing layer 160 may have an acoustic impedance smaller than that of the piezoelectric layer 130. For example, the sound absorbing layer 160 may be made of a material having an acoustic impedance of 2MRayl to 5MRayl. The sound absorbing layer 160 may be formed of a material including rubber to which epoxy resin, tungsten powder, and the like are added. In addition, the sound absorbing layer 160 may be formed of a plurality of layers in order to improve the attenuation or blocking effect of ultrasonic waves.

The matching layers 110 and 120 are provided above the piezoelectric layer 130. The matching layers 110 and 120 may include the first matching layer 120 and the second matching layer 110 having different materials. The matching layers 110 and 120 of the present embodiment may be made of a non-conductive material.

The second matching layer 110 may be disposed above the first matching layer 120. The first matching layer 120 and the second matching layer 110 may reduce loss of ultrasonic waves transmitted to or received from an object by properly matching an acoustic impedance of the piezoelectric layer 130 with an acoustic impedance of the object. The acoustic impedances of the object and the piezoelectric layer 130 may be matched by adjusting physical parameters such as sound speeds, thicknesses, and acoustic impedances of the first matching layer 120 and the second matching layer 110. That is, the first matching layer 120 and the second matching layer 110 may suppress reflection of ultrasonic waves caused by a difference between the acoustic impedance of the object and the acoustic impedance of the piezoelectric layer 130.

FIG. 3 illustrates the matching layers 110 and 120 formed of two layers, but may not be limited thereto. The matching layer may be formed of a single layer, or may be formed of three or more matching layers.

The ultrasonic probe 100 may include a circuit layer 150 and a reflective layer 140.

The circuit layer 150 may be disposed below the piezoelectric layer 130. The circuit layer 150 may be formed of a flexible printed circuit board (FFCB).

The reflective layer 140 (enhanced layer) may be disposed below the piezoelectric layer 130. Specifically, the reflective layer 140 may be disposed between the piezoelectric layer 130 and the circuit layer 150. However, the disclosure is not limited thereto, and the reflective layer 140 may be disposed at various positions.

The reflective layer 140 may reflect and scatter ultrasonic waves generated in the piezoelectric layer 130 and may have conductivity. Accordingly, the reflective layer 140 may reflect ultrasonic waves, which are irradiated to the rear of the piezoelectric layer 130, to the front. The reflective layer 140 may be used in a broadband frequency environment.

The piezoelectric layer 130 includes a first electrode 131 and a second electrode 132. According to the present embodiment, the first electrode 131 is formed on one side of the piezoelectric body and the second electrode 132 is formed on the other side of the piezoelectric body. That is, the first electrode 131 is formed on an upper side of the piezoelectric body and the second electrode 132 is formed on a lower side of the piezoelectric body. These electrodes may be formed of a highly conductive metal such as gold, silver and copper.

One of the electrodes formed on one side and the other side of the piezoelectric layer 130 corresponds to an anode (or signal electrode) of the piezoelectric layer 130, and the other one corresponds to a cathode (or ground electrode) of the piezoelectric layer 130. These electrodes are formed such that the anode and the cathode are separated from each other. The present embodiment exemplifies that the first electrode 131 formed on one side of the piezoelectric layer 130 corresponds to the cathode and the second electrode 132 formed on the other side of the piezoelectric layer 130 corresponds to the anode.

However, the shape of the electrodes provided on the piezoelectric layer 130 is not limited thereto, and at least one of the anode and the cathode may be provided as a round electrode.

The piezoelectric layer 130 includes one or more kerfs 133. The one or more kerfs 133 may be formed as the piezoelectric layer 130 is diced in the lateral direction L.

As the one or more kerfs 133 are formed on the piezoelectric layer 130, the piezoelectric elements of the piezoelectric layer 130 may be provided in a plurality of rows along the elevation direction E. The one or more kerfs 133 formed on the piezoelectric layer 130 may be continuously formed on the reflective layer 140 along the axial direction A.

The first matching layer 120 includes a third electrode 121 and a fourth electrode 122. The third electrode 121 and the fourth electrode 122 formed on the first matching layer 120 may be electrically connected to the piezoelectric layer 130. Specifically, the third electrode 121 and the fourth electrode 122 may be electrically connected to the first electrode 131 of the piezoelectric layer 130.

The first matching layer 120 includes one or more grooves 123. The one or more grooves 123 are connected to the one or more kerfs 133 formed on the piezoelectric layer 130. That is, the one or more grooves 123 may be formed in a corresponding number at positions corresponding to the one or more kerfs 133.

The third electrodes 121 may be formed in inner surfaces of the one or more grooves 123 of the first matching layer 120 to be electrically connected to the first electrode 131 of the piezoelectric layer 130.

A width of the one or more grooves 123 may be formed larger than or equal to a width of the one or more kerfs 133. Accordingly, while the kerfs 133 are formed on the piezoelectric layer 130 by the dicing process, the third electrodes 121 formed on the grooves 123 may be prevented from being damaged. Details on a manufacturing method of the ultrasonic probe 100 will be described later.

A depth of the one or more grooves 123 is formed smaller than the thickness of the first matching layer 120.

The fourth electrode 122 is formed on one surface of the first matching layer 120. Specifically, the fourth electrode 122 is formed on one surface where the first matching layer 120 and the piezoelectric layer 130 are in contact with each other. In other words, the fourth electrode 122 may be formed below the first matching layer 120. Accordingly, the fourth electrode 122 is electrically connected to the first electrode 131 formed above the piezoelectric layer 130.

The third electrode 121 and the fourth electrode 122 may be formed as substantially the same electrode by the same method. Accordingly, the third electrode 121 and the fourth electrode 122 may be electrically connected to each other.

The second electrode 132 formed below the piezoelectric layer 130 may be electrically connected to the circuit layer 150. The circuit layer 150 may include a signal electrode receiving current so that an electric signal may be applied. The reflective layer 140 may be provided between the piezoelectric layer 130 and the circuit layer 150. Because the reflective layer 140 is made of a conductive material, electrical connection between the piezoelectric layer 130 and the circuit layer 150 may be achieved.

Accordingly, both the first electrode 131 and the second electrode 132 of the piezoelectric layer 130 may be electrically connected.

Figure 5:
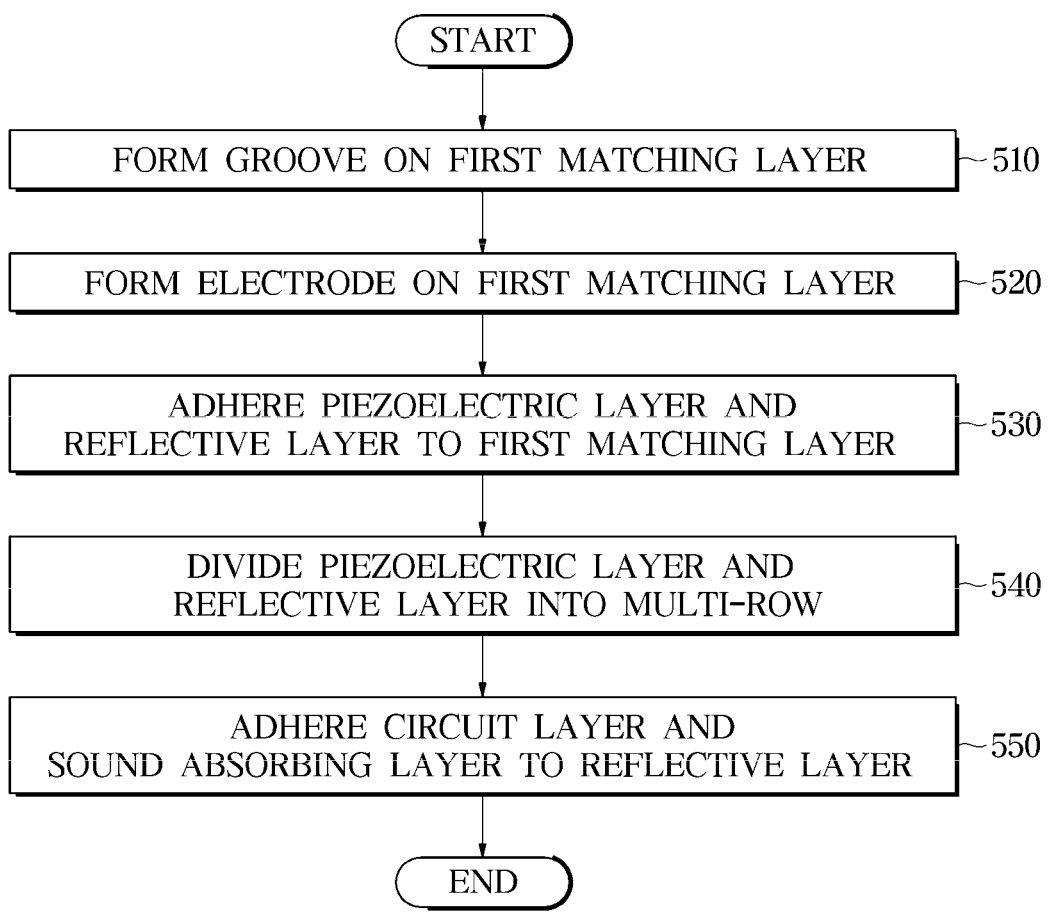
FIG. 5 is a block diagram illustrating a method of manufacturing the ultrasonic probe according to an embodiment of the disclosure.

FIG. 5 is a block diagram illustrating a method of manufacturing the ultrasonic probe according to an embodiment of the disclosure.

Hereinafter, a method of manufacturing the ultrasonic probe 100 according to an embodiment of the disclosure will be described with reference to FIGS. 3 to 5.

In order to manufacture the ultrasonic probe 100 of the present embodiment, the grooves 123 are formed on the first matching layer 120 (510).

The grooves 123 may be provided in a number corresponding to the kerfs 133 to be formed according to rows to be manufactured. Therefore, the one or more grooves 123 may be formed.

Thereafter, the electrodes 121 and 122 are formed on the first matching layer 120 (520).

Specifically, the electrodes 121 and 122 may be formed below the first matching layer 120. In other words, the electrodes 121 and 122 may be formed on a lower surface of the first matching layer 120 and the inner surfaces of the grooves 123. The electrodes 121 and 122 are formed of a highly conductive metal such as gold, silver and copper, and may be made by a sputtering method. However, the disclosure is not limited thereto, and the electrodes 121 and 122 may be made by a method such as deposition, plating, and spray.

The electrode formed in the inner surface of the groove 123 of the first matching layer 120 may be the third electrode 121, and the electrode formed on the lower surface of the first matching layer 120 may be the fourth electrode 122. The lower surface of the first matching layer 120 refers to a surface where the first matching layer 120 and the piezoelectric layer 130 come into contact with each other.

The third electrode 121 may be electrically connected to the first electrode 131 of the piezoelectric layer 130. The fourth electrode 122 may be electrically connected to the first electrode 131 of the piezoelectric layer 130. That is, the third electrode 121 and the fourth electrode 122 may be electrically connected to each other. The third electrode 121 and the fourth electrode 122 are formed at the same time on the first matching layer 120, and thus the electrodes may be provided as substantially the same electrodes.

Thereafter, the piezoelectric layer 130 and the reflective layer 140 are adhered to the first matching layer 120 (530).

Specifically, the piezoelectric layer 130 may be adhered to the lower surface of the first matching layer 120 and the reflective layer 140 may be adhered to a lower surface of the piezoelectric layer 130.

Thereafter, the piezoelectric layer 130 and the reflective layer 140 are divided into a plurality of rows (540).

Specifically, the kerf 133 corresponding to the position of the groove 123 is formed on the piezoelectric layer 130 so that the piezoelectric layer 130 is divided into a plurality of rows along the elevation direction E. The kerf 133 may be formed by a process in which the piezoelectric layer 130 is diced in the lateral direction L.

The one or more grooves 123 and the one or more kerfs 133 formed at the positions corresponding thereto may be connected to each other. The width of the groove 123 may be formed larger than or equal to the width of the kerf 133. Because the size of the ultrasonic probe 100 is small, the third electrode 121 and the fourth electrode 122 formed on the first matching layer 120 may be diced together in the process of dicing the piezoelectric layer 130 to form the kerf 133. Accordingly, by forming the width of the groove 123 as described above, damage to the third electrode 121 and the fourth electrode 122 of the first matching layer 120 during the dicing process may be prevented.

Thereafter, the circuit layer 150 and the sound absorbing layer 160 are adhered to the reflective layer 140 (550).

Specifically, the circuit layer 150 may be adhered to a lower surface of the reflective layer 140 to be electrically connected to the second electrode 132 of the piezoelectric layer 130. Because the reflective layer 140 is made of a conductive material, electrical connection between the second electrode 132 and the circuit layer 150 may be secured. The circuit layer 150 may be provided as a flexible printed circuit board. Also, the sound absorbing layer 160 may be adhered to a lower surface of the circuit layer 150.

According to the manufacturing method of the ultrasonic probe 100 of the present embodiment as described above, electrical connection may be easily achieved without using a conductive matching layer, thereby reducing the manufacturing cost. In addition, while the conductive matching layer is made of carbon and thus may be vulnerable to an external impact, a probe resistant to an external impact may be produced by using a non-conductive matching layer.

In addition, because it is not necessary to use a separate printed circuit board in order to electrically connect the ground electrode of the piezoelectric layer 130, the performance of the ultrasonic probe 100 may be secured even in a high frequency environment.

In addition, because the piezoelectric layer 130 is diced after the grooves 123 and the electrodes are formed on the first matching layer 120, an electrical connection method applicable even to a multi-row probe structure may be provided.

Figure 6:
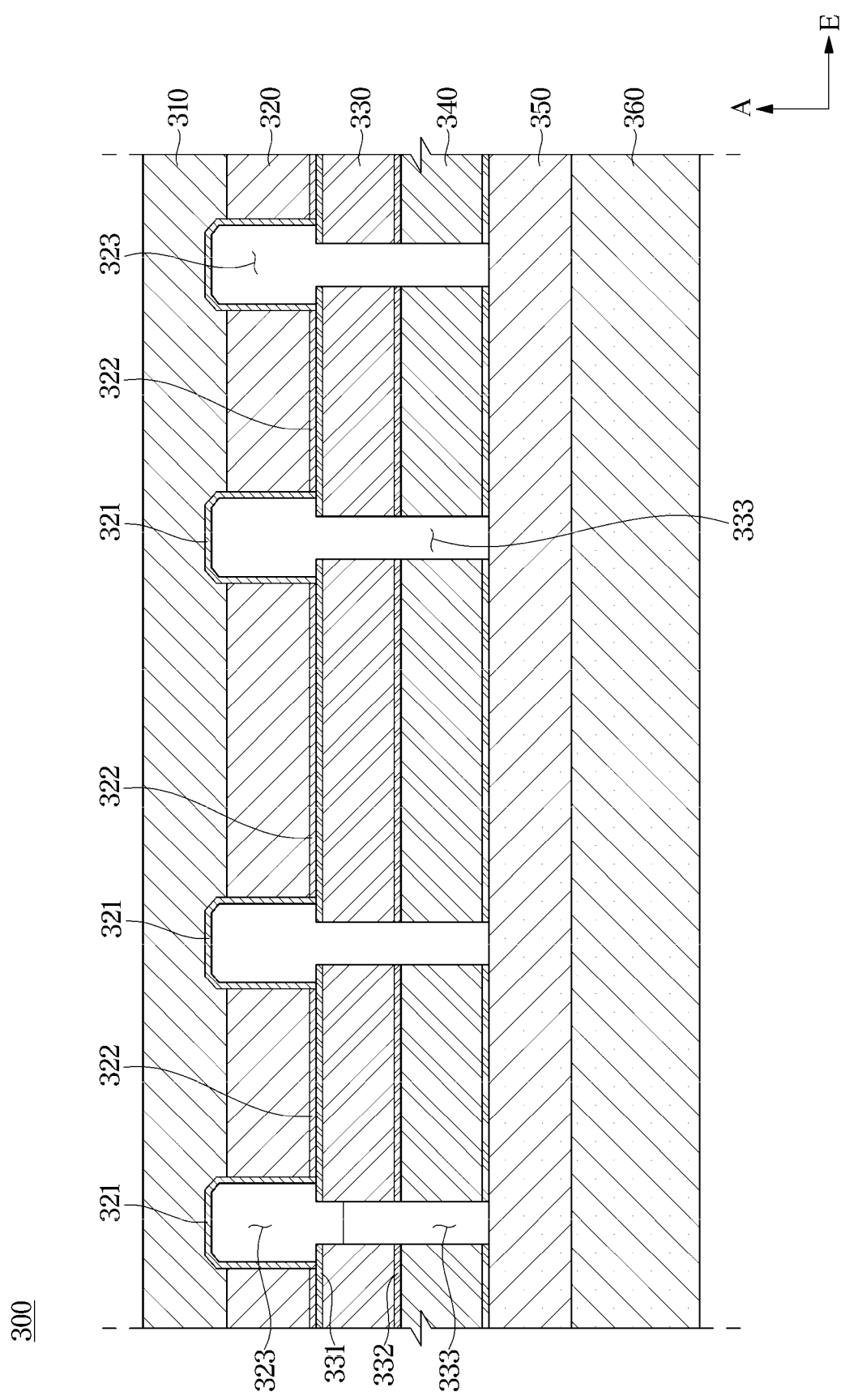
FIG. 6 is a cross-sectional view taken along an axis direction and an elevation direction of an ultrasonic probe according to another embodiment of the disclosure.
Figure 7:
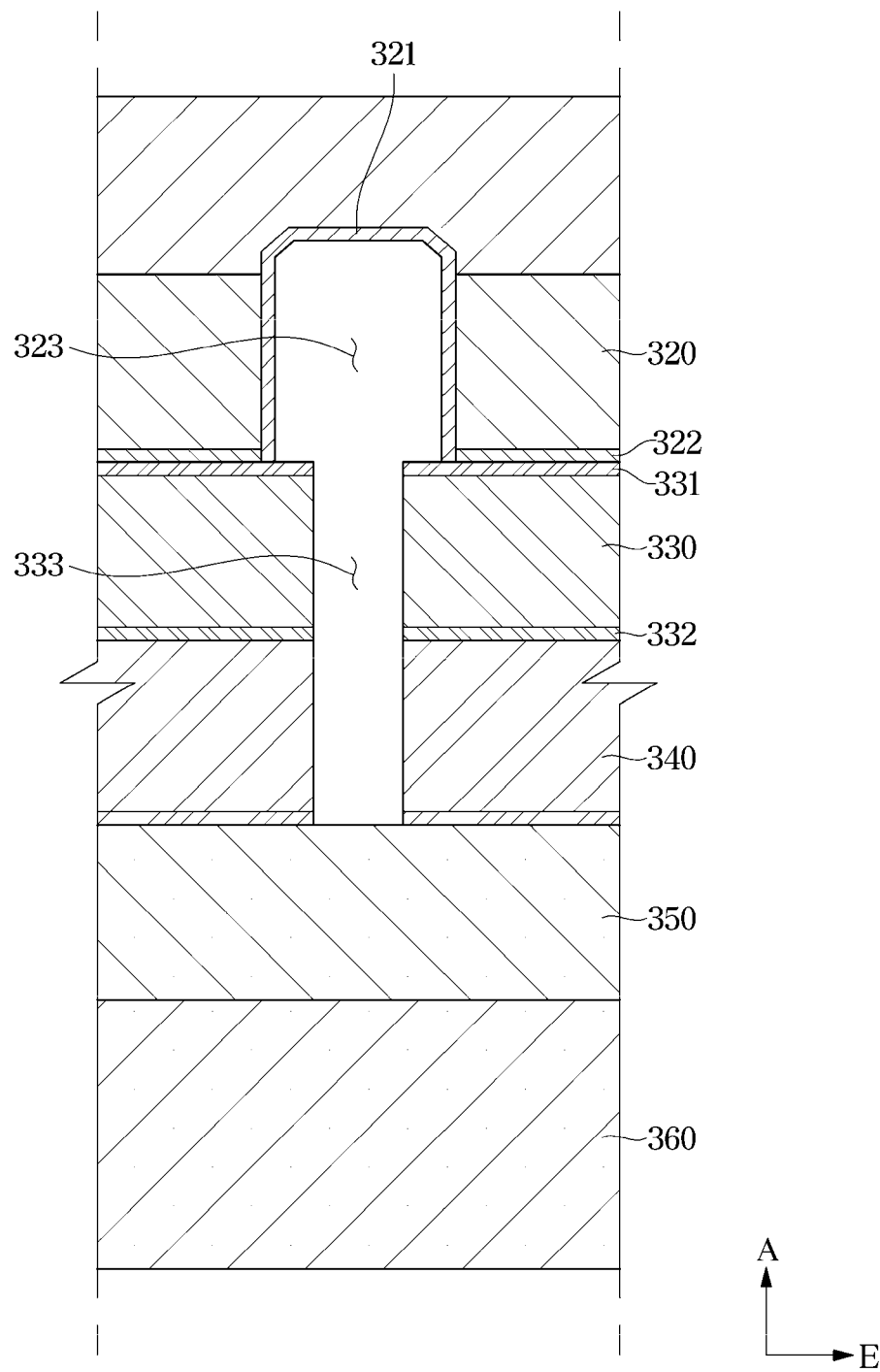
FIG. 7 is an enlarged view of a partial area in FIG. 6.

FIG. 6 is a cross-sectional view taken along an axis direction and an elevation direction of an ultrasonic probe according to another embodiment of the disclosure, and FIG. 7 is an enlarged view of a partial area in FIG. 6.

Referring to FIGS. 6 and 7, an ultrasonic probe 300 includes a piezoelectric layer 330, a sound absorbing layer 360 provided below the piezoelectric layer 330, and matching layers 310 and 320 provided above the piezoelectric layer 330.

The piezoelectric layer 330 may irradiate mechanical vibration energy as ultrasonic waves in a direction in which a lens is provided and a direction in which the sound absorbing layer 360 is provided. Hereinafter the direction in which the lens is provided is referred to as the front and the direction in which the sound absorbing layer 360 is provided is referred to as the rear, based on the piezoelectric layer 330.

The piezoelectric layer 330 may be processed in the form of a multidimensional array of the form of a matrix forming a plurality of rows by a dicing process.

The sound absorbing layer 360 is disposed below the piezoelectric layer 330 and absorbs ultrasonic waves that are generated in the piezoelectric layer 330 and proceed backward, thereby blocking the ultrasonic waves from proceeding to the rear of the piezoelectric layer 330. Therefore, images may be prevented from being distorted.

The sound absorbing layer 360 may have an acoustic impedance smaller than that of the piezoelectric layer 330. For example, the sound absorbing layer 360 may be made of a material having an acoustic impedance of 2MRay1 to 5MRay1. The sound absorbing layer 360 may be formed of a material including rubber to which epoxy resin, tungsten powder, and the like are added. In addition, the sound absorbing layer 360 may be formed of a plurality of layers in order to improve the attenuation or blocking effect of ultrasonic waves.

The matching layers 310 and 320 are provided above the piezoelectric layer 330. The matching layers 310 and 320 may include the first matching layer 320 and the second matching layer 310 having different materials. The matching layers 310 and 320 of the present embodiment may be made of a non-conductive material.

The second matching layer 310 may be disposed above the first matching layer 320. The first matching layer 320 and the second matching layer 310 may reduce loss of ultrasonic waves transmitted to or received from an object by properly matching an acoustic impedance of the piezoelectric layer 330 with an acoustic impedance of the object. The acoustic impedances of the object and the piezoelectric layer 330 may be matched by adjusting physical parameters such as sound speeds, thicknesses, and acoustic impedances of the first matching layer 320 and the second matching layer 310. That is, the first matching layer 320 and the second matching layer 310 may suppress reflection of ultrasonic waves caused by a difference between the acoustic impedance of the object and the acoustic impedance of the piezoelectric layer 330.

The ultrasonic probe 300 may include a circuit layer 350 and a reflective layer 340.

The circuit layer 350 may be disposed below the piezoelectric layer 330. The circuit layer 350 may be formed of a flexible printed circuit board (FPCB).

The reflective layer 340 (enhanced layer) may be disposed below the piezoelectric layer 330. Specifically, the reflective layer 340 may be disposed between the piezoelectric layer 330 and the circuit layer 350. The reflective layer 340 may reflect and scatter ultrasonic waves generated in the piezoelectric layer 330 and may have conductivity. Accordingly, the reflective layer 340 may reflect ultrasonic waves, which are irradiated to the rear of the piezoelectric layer 330, to the front. The reflective layer 340 may be used in a broadband frequency environment. However, the disclosure is not limited thereto, and the reflective layer 340 may be disposed at various positions.

The piezoelectric layer 330 includes a first electrode 331 and a second electrode 332. According to the present embodiment, the first electrode 331 is formed on one side of the piezoelectric body and the second electrode 332 is formed on the other side of the piezoelectric body. That is, the first electrode 331 is formed on an upper side of the piezoelectric body and the second electrode 332 is formed on a lower side of the piezoelectric body. These electrodes may be formed of a highly conductive metal such as gold, silver and copper.

One of the electrodes formed on one side and the other side of the piezoelectric layer 330 corresponds to an anode (or signal electrode) of the piezoelectric layer 330, and the other one corresponds to a cathode (or ground electrode) of the piezoelectric layer 330. These electrodes are formed such that the anode and the cathode are separated from each other. The present embodiment exemplifies that the first electrode 331 formed on one side of the piezoelectric layer 330 corresponds to the cathode and the second electrode 332 formed on the other side of the piezoelectric layer 330 corresponds to the anode.

However, the shape of the electrodes provided on the piezoelectric layer 330 is not limited thereto, and at least one of the anode and the cathode may be provided as a round electrode.

The piezoelectric layer 330 includes one or more kerfs 333. The one or more kerfs 333 may be formed as the piezoelectric layer 330 is diced in the lateral direction L. As the one or more kerfs 333 are formed on the piezoelectric layer 330, piezoelectric elements of the piezoelectric layer 330 may be provided in a plurality of rows along the elevation direction E. The one or more kerfs 333 formed on the piezoelectric layer 330 may be continuously formed on the reflective layer 340 along the axial direction A.

A difference between the ultrasonic probe 100 according to an embodiment of the disclosure and the ultrasonic probe 300 according to another embodiment is that the first matching layer 320 and the second matching layer 310 include a third electrode 321 and the first matching layer 320 includes a fourth electrode 322. That is, the third electrode 321 may also be formed on the second matching layer 310.

The third electrode 321 and the fourth electrode 322 formed on the first matching layer 320 and the second matching layer 310 may be electrically connected to the piezoelectric layer 330. Specifically, the third electrode 321 and the fourth electrode 322 may be electrically connected to the first electrode 331 of the piezoelectric layer 330.

The first matching layer 320 and the second matching layer 310 include one or more grooves 323. The one or more grooves 323 are connected to the one or more kerfs 333 formed on the piezoelectric layer 330. That is, the one or more grooves 323 may be formed in a corresponding number at positions corresponding to the one or more kerfs 333.

The third electrodes 321 may be formed in inner surfaces of the one or more grooves 323 to be electrically connected to the first electrode 331 of the piezoelectric layer 330.

A width of the one or more grooves 323 may be formed larger than or equal to a width of the one or more kerfs 333. Accordingly, while the kerfs 333 are formed on the piezoelectric layer 330 by the dicing process, the third electrodes 321 formed on the grooves 323 may be prevented from being damaged. Details on a manufacturing method of the ultrasonic probe 300 will be described later.

Unlike the ultrasonic probe 100 according to an embodiment of the disclosure, a depth of the one or more grooves 323 may be formed larger than a thickness of the first matching layer 320 and smaller than the combined thickness of the first matching layer 320 and the second matching layer 310.

The fourth electrode 322 is formed on one surface of the first matching layer 320. Specifically, the fourth electrode 322 is formed on one surface where the first matching layer 320 and the piezoelectric layer 330 are in contact with each other. In other words, the fourth electrode 322 may be formed below the first matching layer 320. Accordingly, the fourth electrode 322 is electrically connected to the first electrode 331 formed above the piezoelectric layer 330.

The third electrode 321 and the fourth electrode 322 may be formed as substantially the same electrode by the same method. Accordingly, the third electrode 321 and the fourth electrode 322 may be electrically connected to each other.

FIGS. 1 and 2 illustrate that the ultrasonic probe 100 according to an embodiment of the disclosure is provided, but may also be applied to the ultrasonic probe 300 according to another embodiment of the disclosure.

Figure 8:
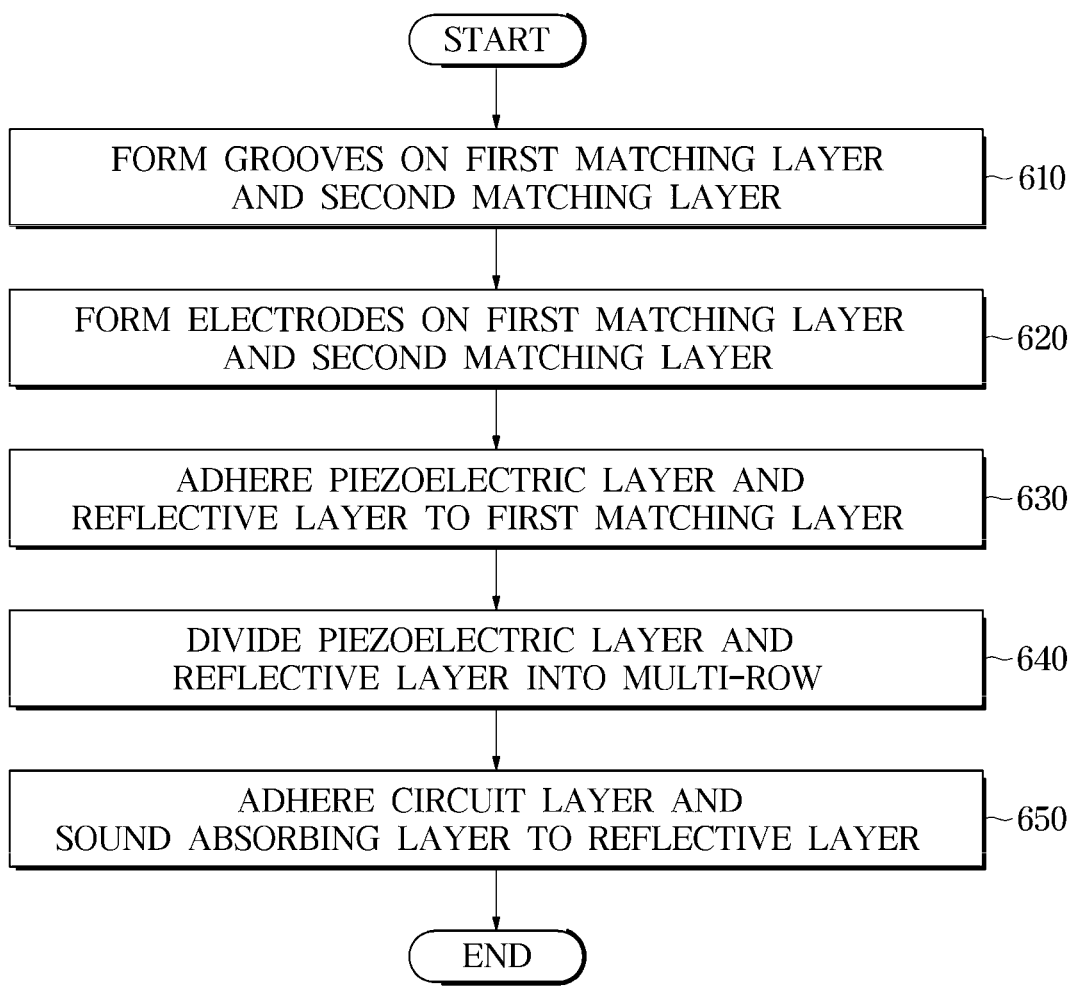
FIG. 8 is a block diagram illustrating a method of manufacturing the ultrasonic probe according to another embodiment of the disclosure.

FIG. 8 is a block diagram illustrating a method of manufacturing the ultrasonic probe according to another embodiment of the disclosure.

Hereinafter, a method of manufacturing the ultrasonic probe 300 according to another embodiment of the disclosure will be described with reference to FIGS. 6 to 8.

In order to manufacture the ultrasonic probe 300 of the present embodiment, the grooves 323 are formed on the first matching layer 320 and the second matching layer 310 (610).

The grooves 323 may be provided in a number corresponding to the kerfs 333 to be formed according to rows to be manufactured. Therefore, the one or more grooves 323 may be formed.

Thereafter, the electrodes 321 and 322 are formed on the first matching layer 320 and the second matching layer 310 (620).

Specifically, the electrodes 321 and 322 may be formed below the first matching layer 320. In other words, the electrodes 321 and 322 may be formed on a lower surface of the first matching layer 320 and the inner surfaces of the grooves 323. The electrodes 321 and 322 are formed of a highly conductive metal such as gold, silver and copper, and may be made by a sputtering method. However, the disclosure is not limited thereto, and the electrodes 321 and 322 may be made by a method such as deposition, plating, and spray.

The electrodes formed in the inner surfaces of the grooves 323 of the first matching layer 320 and the second matching layer 310 may be the third electrodes 321, and the electrode formed on the lower surface of the first matching layer 320 may be the fourth electrode 322. The lower surface of the first matching layer 320 refers to a surface where the first matching layer 320 and the piezoelectric layer 330 come into contact with each other.

The third electrode 321 may be electrically connected to the first electrode 331 of the piezoelectric layer 330. The fourth electrode 322 may be electrically connected to the first electrode 331 of the piezoelectric layer 330. That is, the third electrode 321 and the fourth electrode 322 may be electrically connected to each other. The third electrodes 321 are formed on the first matching layer 120 and the second matching layer 310 and at the same time the fourth electrode 322 is formed on the first matching layer 320, so that the electrodes may be provided as substantially the same electrodes.

Thereafter, the piezoelectric layer 330 and the reflective layer 340 are adhered to the first matching layer 320 (630).

Specifically, the piezoelectric layer 330 may be adhered to the lower surface of the first matching layer 320 and the reflective layer 340 may be adhered to a lower surface of the piezoelectric layer 330.

Thereafter, the piezoelectric layer 330 and the reflective layer 340 are divided into a plurality of rows (640).

Specifically, the kerf 333 corresponding to the position of the groove 323 is formed on the piezoelectric layer 330 so that the piezoelectric layer 330 is divided into a plurality of rows along the elevation direction E. The kerf 333 may be formed by a process in which the piezoelectric layer 330 is diced in the lateral direction L.

The one or more grooves 323 and the one or more kerfs 333 formed at the positions corresponding thereto may be connected to each other. The width of the groove 323 may be formed larger than or equal to the width of the kerf 333. Because the size of the ultrasonic probe 300 is small, the third electrode 321 and the fourth electrode 322 formed on the first matching layer 320 may be diced together in the process of dicing the piezoelectric layer 330 to form the ken 333. Accordingly, by forming the width of the groove 323 as described above, damage to the third electrode 321 and the fourth electrode 322 of the first matching layer 320 during the dicing process may be prevented.

Thereafter, the circuit layer 350 and the sound absorbing layer 360 are adhered to the reflective layer 340 (650).

Specifically, the circuit layer 350 may be adhered to a lower surface of the reflective layer 340 to be electrically connected to the second electrode 332 of the piezoelectric layer 330. Because the reflective layer 340 is made of a conductive material, electrical connection between the second electrode 332 and the circuit layer 350 may be secured. The circuit layer 350 may be provided as a flexible printed circuit board. Also, the sound absorbing layer 360 may be adhered to a lower surface of the circuit layer 350.

According to the manufacturing method of the ultrasonic probe 300 of the present embodiment as described above, electrical connection may be easily achieved without using a conductive matching layer, thereby reducing the manufacturing cost. In addition, while the conductive matching layer is made of carbon and thus may be vulnerable to an external impact, a probe resistant to an external impact may be produced by using a non-conductive matching layer.

In addition, because it is not necessary to use a separate printed circuit board in order to electrically connect the ground electrode of the piezoelectric layer 330, the performance of the ultrasonic probe 300 may be secured even in a high frequency environment.

In addition, because the piezoelectric layer 330 is diced after the grooves 323 and the electrodes 321 and 322 are formed on the first matching layer 320 and the second matching layer 310, an electrical connection method applicable even to a multi-row probe structure may be provided.

Figure 9:
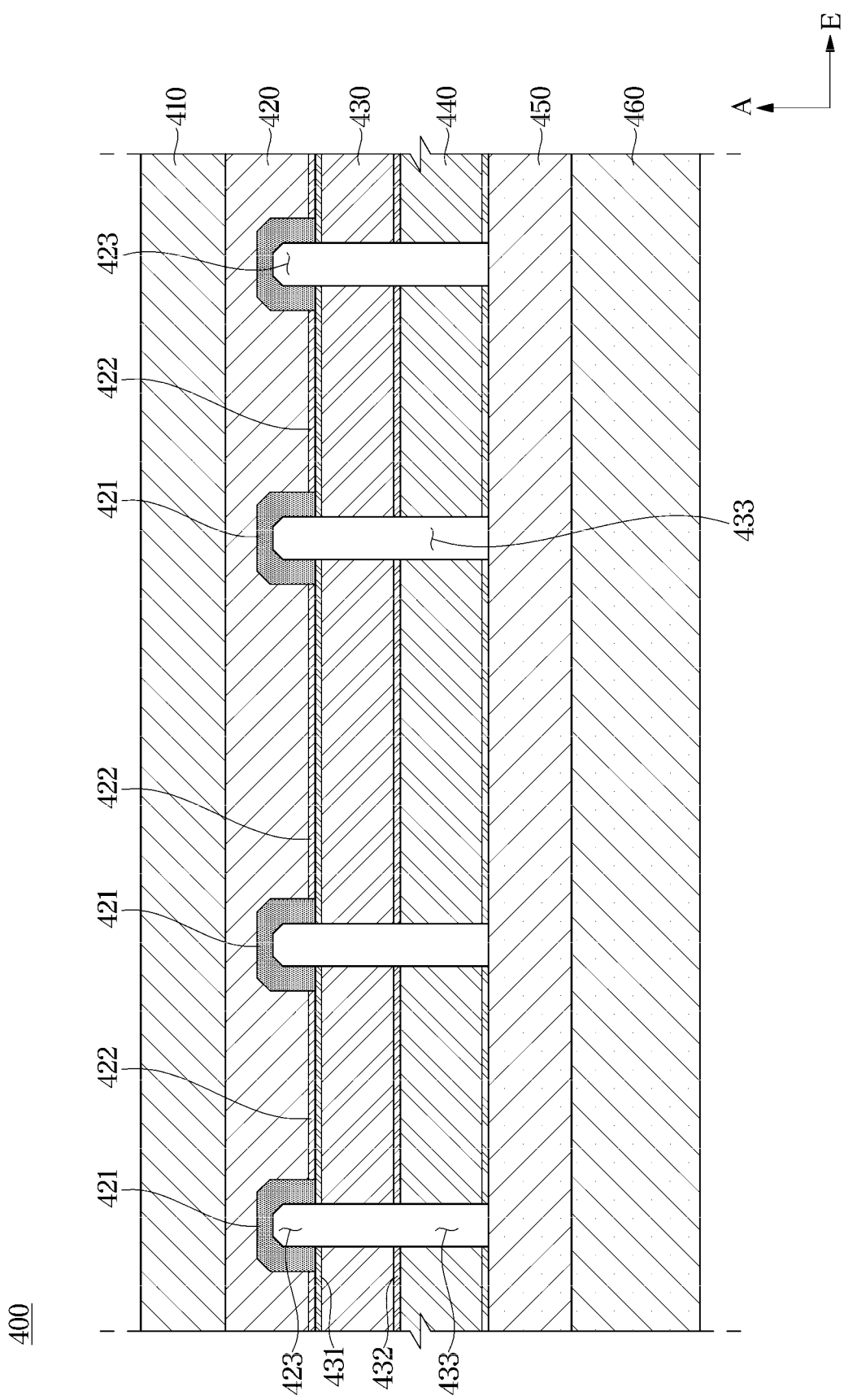
FIG. 9 is a cross-sectional view taken along an axis direction and an elevation direction of an ultrasonic probe according to another embodiment of the disclosure.
Figure 10:
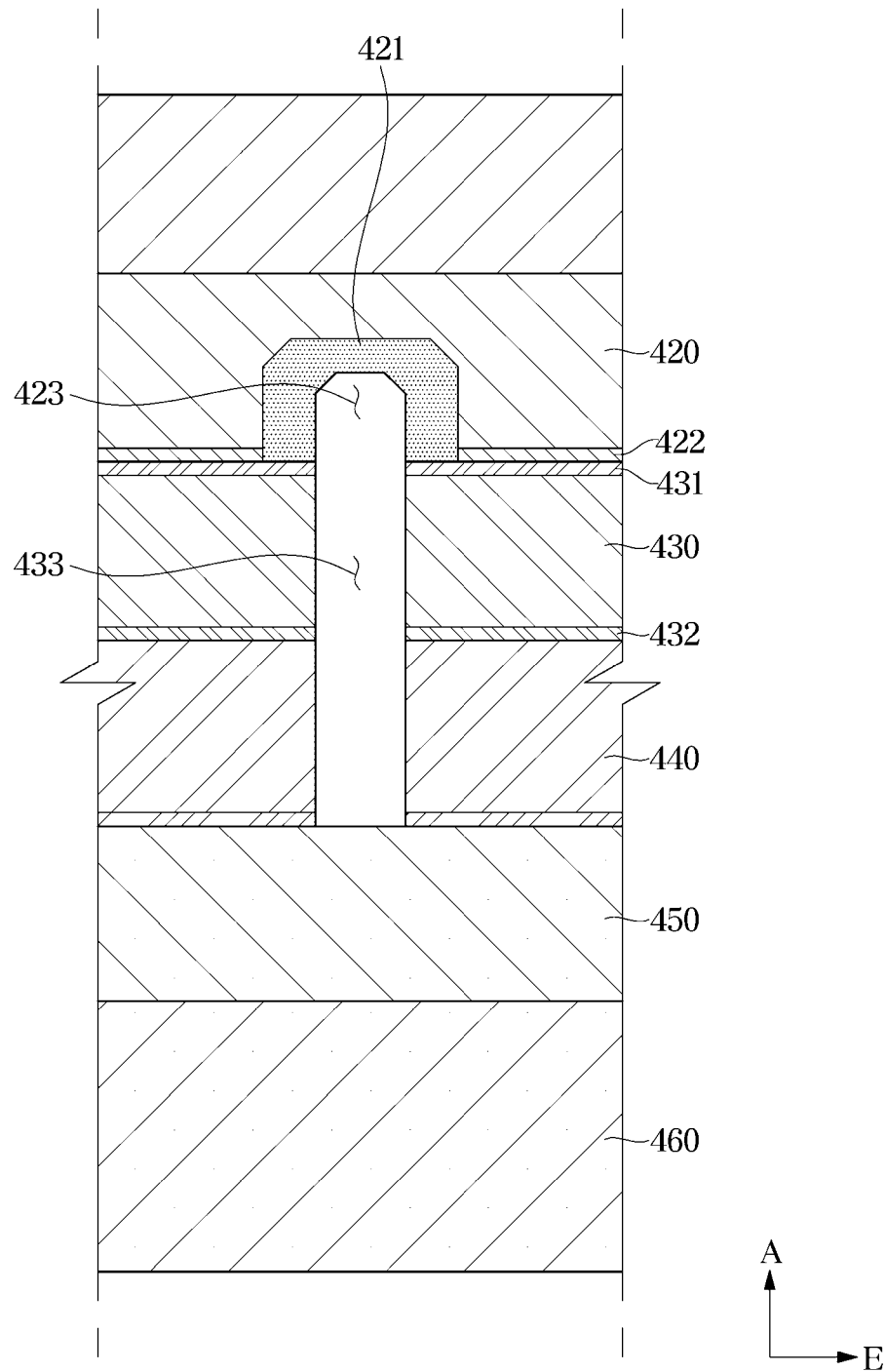
FIG. 10 is an enlarged view of a partial area in FIG. 9.

FIG. 9 is a cross-sectional view taken along an axis direction and an elevation direction of an ultrasonic probe according to another embodiment of the disclosure, and FIG. 10 is an enlarged view of a partial area in FIG. 9.

Referring to FIGS. 9 and 10, an ultrasonic probe 400 includes a piezoelectric layer 430, a sound absorbing layer 460 provided below the piezoelectric layer 430, and matching layers 410 and 420 provided above the piezoelectric layer 430.

The piezoelectric layer 430 may irradiate mechanical vibration energy as ultrasonic waves in a direction in which a lens is provided and a direction in which the sound absorbing layer 460 is provided. Hereinafter the direction in which the lens is provided is referred to as the front and the direction in which the sound absorbing layer 460 is provided is referred to as the rear, based on the piezoelectric layer 430.

The piezoelectric layer 430 may be processed in the form of a multidimensional array of the form of a matrix forming a plurality of rows by a dicing process.

The sound absorbing layer 460 is disposed below the piezoelectric layer 430 and absorbs ultrasonic waves that are generated in the piezoelectric layer 430 and proceed backward, thereby blocking the ultrasonic waves from proceeding to the rear of the piezoelectric layer 430. Therefore, images may be prevented from being distorted.

The sound absorbing layer 460 may have an acoustic impedance smaller than that of the piezoelectric layer 430. For example, the sound absorbing layer 460 may be made of a material having an acoustic impedance of 2MRay1 to 5MRay1. The sound absorbing layer 460 may be formed of a material including rubber to which epoxy resin, tungsten powder, and the like are added. In addition, the sound absorbing layer 460 may be formed of a plurality of layers in order to improve the attenuation or blocking effect of ultrasonic waves.

The matching layers 410 and 420 are provided above the piezoelectric layer 430. The matching layers 410 and 420 may include the first matching layer 420 and the second matching layer 410 having different materials. The matching layers 410 and 420 of the present embodiment may be made of a non-conductive material.

The second matching layer 410 may be disposed above the first matching layer 420. The first matching layer 420 and the second matching layer 410 may reduce loss of ultrasonic waves transmitted to or received from an object by properly matching an acoustic impedance of the piezoelectric layer 430 with an acoustic impedance of the object. The acoustic impedances of the object and the piezoelectric layer 430 may be matched by adjusting physical parameters such as sound speeds, thicknesses, and acoustic impedances of the first matching layer 420 and the second matching layer 410. That is, the first matching layer 420 and the second matching layer 410 may suppress reflection of ultrasonic waves caused by a difference between the acoustic impedance of the object and the acoustic impedance of the piezoelectric layer 430.

The ultrasonic probe 400 may include a circuit layer 450 and a reflective layer 440.

The circuit layer 450 may be disposed below the piezoelectric layer 430. The circuit layer 450 may be formed of a flexible printed circuit board (FPCB).

The reflective layer 440 (enhanced layer) may be disposed below the piezoelectric layer 430. Specifically, the reflective layer 440 may be disposed between the piezoelectric layer 430 and the circuit layer 450. The reflective layer 440 may reflect and scatter ultrasonic waves generated in the piezoelectric layer 430 and may have conductivity. Accordingly, the reflective layer 440 may reflect ultrasonic waves, which are irradiated to the rear of the piezoelectric layer 430, to the front. The reflective layer 440 may be used in a broadband frequency environment. However, the disclosure is not limited thereto, and the reflective layer 440 may be disposed at various positions.

The piezoelectric layer 430 includes a first electrode 431 and a second electrode 432. According to the present embodiment, the first electrode 431 is formed on one side of the piezoelectric body and the second electrode 432 is formed on the other side of the piezoelectric body. That is, the first electrode 431 is formed on an upper side of the piezoelectric body and the second electrode 432 is formed on a lower side of the piezoelectric body. These electrodes may be formed of a highly conductive metal such as gold, silver and copper.

One of the electrodes formed on one side and the other side of the piezoelectric layer 430 corresponds to an anode (or signal electrode) of the piezoelectric layer 430, and the other one corresponds to a cathode (or ground electrode) of the piezoelectric layer 430. These electrodes are formed such that the anode and the cathode are separated from each other. The present embodiment exemplifies that the first electrode 431 formed on one side of the piezoelectric layer 430 corresponds to the cathode and the second electrode 432 formed on the other side of the piezoelectric layer 430 corresponds to the anode.

However, the shape of the electrodes provided on the piezoelectric layer 430 is not limited thereto, and at least one of the anode and the cathode may be provided as a round electrode.

The piezoelectric layer 430 includes one or more kerfs 433. The one or more kerfs 433 may be formed as the piezoelectric layer 430 is diced in the lateral direction L. As the one or more kerfs 433 are formed on the piezoelectric layer 430, piezoelectric elements of the piezoelectric layer 430 may be provided in a plurality of rows along the elevation direction E. The one or more kerfs 433 formed on the piezoelectric layer 430 may be continuously formed on the reflective layer 440 along the axial direction A.

In the ultrasonic probe 400 according to another embodiment of the disclosure, a third electrode 421 is formed by filling a groove 423 formed on the first matching layer 420 with a conductive material.

The third electrode 421 formed on the groove 423 of the first matching layer 420 and a fourth electrode 422 formed on a lower surface of the first matching layer 420 may be electrically connected to the piezoelectric layer 430. Specifically, the third electrode 421 and the fourth electrode 422 may be electrically connected to the first electrode 431 of the piezoelectric layer 430.

The first matching layer 420 includes one or more grooves 423. The one or more grooves 423 are connected to the one or more kerfs 433 formed on the piezoelectric layer 430. That is, the one or more grooves 423 may be formed in a corresponding number at positions corresponding to the one or more kerfs 433.

The third electrode 421 may be formed by filling the one or more grooves 423 with a conductive material. The third electrode 421 may be electrically connected to the first electrode 431 of the piezoelectric layer 430.

A width of the one or more grooves 423 may be formed larger than or equal to a width of the one or more kerfs 433. Accordingly, while the kerfs 433 are formed on the piezoelectric layer 430 by the dicing process, the third electrodes 421 formed on the grooves 423 may be prevented from being damaged and from disconnecting the electrical connection, Details on a manufacturing method of the ultrasonic probe 400 will be described later.

A depth of the one or more grooves 423 may be formed smaller than or equal to the thickness of the first matching layer 420.

FIGS. 9 and 10 illustrate that the grooves 423 are formed only on the first matching layer 420. However, the disclosure is not limited thereto, and a depth of the one or more grooves 423 may be formed larger than a thickness of the first matching layer 420 and smaller than the combined thickness of the first matching layer 420 and the second matching layer 410. That is, the grooves 423 may also be formed on the second matching layer 410.

The fourth electrode 422 is formed on one surface of the first matching layer 420. Specifically, the fourth electrode 422 is formed on one surface where the first matching layer 420 and the piezoelectric layer 430 are in contact with each other. In other words, the fourth electrode 422 may be formed below the first matching layer 420. Accordingly, the fourth electrode 422 is electrically connected to the first electrode 431 formed above the piezoelectric layer 430.

The third electrode 421 and the fourth electrode 422 may also be electrically connected to each other.

In the ultrasonic probe 400 according to another embodiment of the disclosure, because an electrode is formed by filling a conductive material in the groove 423, an area capable of being electrically connected to the piezoelectric layer 430 may be secured more widely.

FIGS. 1 and 2 illustrate that the ultrasonic probe 100 according to an embodiment of the disclosure is provided, but may also be applied to the ultrasonic probe 400 according to another embodiment of the disclosure.

Figure 11:
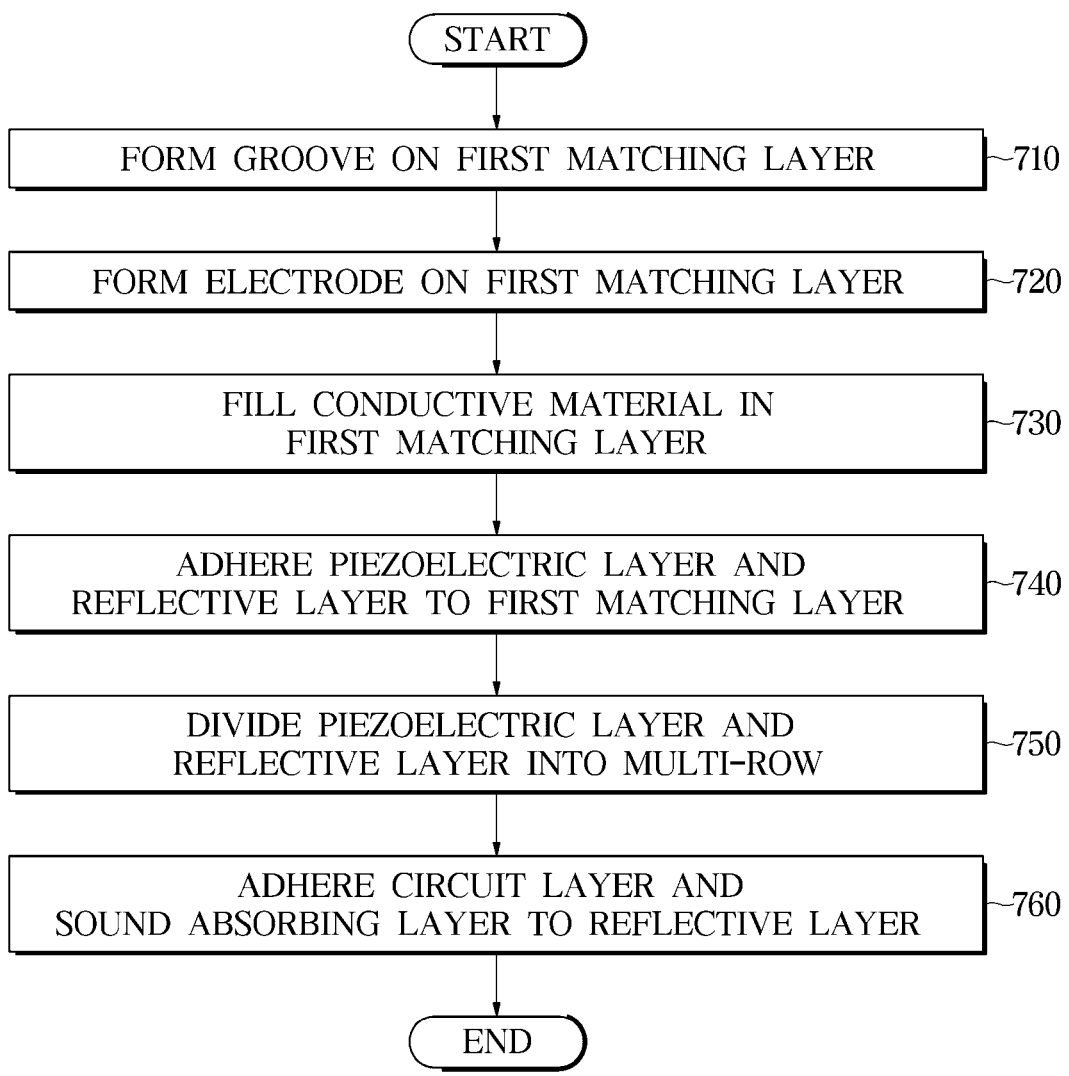
FIG. 11 is a block diagram illustrating a method of manufacturing the ultrasonic probe according to another embodiment of the disclosure.

FIG. 11 is a block diagram illustrating a method of manufacturing the ultrasonic probe according to another embodiment of the disclosure.

Hereinafter, a method of manufacturing the ultrasonic probe 400 according to another embodiment of the disclosure will be described with reference to FIGS. 9 to 11.

In order to manufacture the ultrasonic probe 400 of the present embodiment, the grooves 423 are formed on the first matching layer 420 (710).

The grooves 423 may be provided in a number corresponding to the kerfs 433 to be formed according to rows to be manufactured. Therefore, the one or more grooves 423 may be formed.

Thereafter, the electrodes are formed on the first matching layer 420 (720).

Specifically, the electrodes may be formed below the first matching layer 420. In other words, the electrodes may be formed on the lower surface of the first matching layer 420 and inner surfaces of the grooves 423. The electrodes are formed of a highly conductive metal such as gold, silver and copper, and may be made by a sputtering method. However, the disclosure is not limited thereto, and the electrodes may be made by a method such as deposition, plating, and spray.

Thereafter, a conductive material is filled in the grooves 423 of the first matching layer 420 (730).

The conductive material filled in the grooves 423 of the first matching layer 420 may be the third electrode 421, and the electrode formed on the lower surface of the first matching layer 420 may be the fourth electrode 422. The lower surface of the first matching layer 420 refers to a surface where the first matching layer 420 and the piezoelectric layer 430 come into contact with each other.

Accordingly, the third electrode 421 and the fourth electrode 422 of the ultrasonic probe 400 according to the present embodiment may be formed in different manners.

The third electrode 421 may be electrically connected to the first electrode 431 of the piezoelectric layer 430. The fourth electrode 422 may be electrically connected to the first electrode 431 of the piezoelectric layer 430. That is, the third electrode 421 and the fourth electrode 422 may be electrically connected to each other.

Thereafter, the piezoelectric layer 430 and the reflective layer 440 are adhered to the first matching layer 420 (740).

Specifically, the piezoelectric layer 430 may be adhered to the lower surface of the first matching layer 420 and the reflective layer 440 may be adhered to a lower surface of the piezoelectric layer 430.

Thereafter, the piezoelectric layer 430 and the reflective layer 440 are divided into a plurality of rows (750).

Specifically, the kerf 433 corresponding to the position of the groove 423 is formed on the piezoelectric layer 430 so that the piezoelectric layer 430 is divided into a plurality of rows along the elevation direction E. The kerf 433 may be formed by a process in which the piezoelectric layer 430 is diced in the lateral direction L.

The one or more grooves 423 and the one or more kerfs 433 formed at the positions corresponding thereto may be connected to each other. The width of the groove 423 may be formed larger than or equal to the width of the kerf 433. Because the size of the ultrasonic probe 400 is small, the third electrode 421 and the fourth electrode 422 formed on the first matching layer 420 may be diced together in the process of dicing the piezoelectric layer 430 to form the kerf 433. Accordingly, by forming the width of the groove 423 as described above, damage to the third electrode 421 and the fourth electrode 422 of the first matching layer 420 during the dicing process may be prevented.

However, according to the manufacturing method of the ultrasonic probe 400 according to another embodiment of the disclosure, because the third electrode 421 is formed by filling a conductive material in the groove 423, even when a portion of the third electrode 421 is damaged by the above-described dicing process, the electrical connection with the piezoelectric layer 430 may be secured more reliably.

Thereafter, the circuit layer 450 and the sound absorbing layer 460 are adhered to the reflective layer 440 (760).

Specifically, the circuit layer 450 may be adhered to a lower surface of the reflective layer 440 to be electrically connected to the second electrode 432 of the piezoelectric layer 430. Because the reflective layer 440 is made of a conductive material, electrical connection between the second electrode 432 and the circuit layer 450 may be secured. The circuit layer 450 may be provided as a flexible printed circuit board. Also, the sound absorbing layer 460 may be adhered to a lower surface of the circuit layer 450.

According to the manufacturing method of the ultrasonic probe 400 of the present embodiment as described above, electrical connection may be easily achieved without using a conductive matching layer, thereby reducing the manufacturing cost. In addition, while the conductive matching layer is made of carbon and thus may be vulnerable to an external impact, a probe resistant to an external impact may be produced by using a non-conductive matching layer.

In addition, because it is not necessary to use a separate printed circuit board in order to electrically connect the ground electrode of the piezoelectric layer 430, the performance of the ultrasonic probe 400 may be secured even in a high frequency environment.

In addition, because the piezoelectric layer 430 is diced after the grooves 423 and the electrodes are formed on the first matching layer 420, an electrical connection method applicable even to a multi-row probe structure may be provided.

FIGS. 9 to 11 illustrate that the third electrodes 421 are formed by filling the grooves 423 formed in the first matching layer 420 with a conductive material. However, the disclosure is not limited thereto, and the third electrodes 421 may be formed by filling the grooves 423 formed in both the first matching layer 420 and the second matching layer 410 with a conductive material.

As is apparent from the above, an electrode is formed on a matching layer as a thin film, a signal from an ultrasonic probe can be accurately transmitted even in a high frequency environment.

Further, a groove is formed inside the matching layer, so that damage to the electrode of the matching layer in a process of dicing for a multi-row probe can be prevented.

Further, by using a conventional non-conductive matching layer, the manufacturing cost of the ultrasonic probe can be reduced.

The foregoing has illustrated and described specific embodiments. However, it should be understood by those of skilled in the art that the disclosure is not limited to the above-described embodiments, and various changes and modifications may be made without departing from the technical idea of the disclosure described in the following claims.

What is claimed is:

1. An ultrasonic probe comprising:
a piezoelectric layer comprising one or more kerfs such that piezoelectric elements are provided in a plurality of rows along an elevation direction;
a first electrode formed on an upper side of the piezoelectric layer;
a second electrode formed on a lower side of the piezoelectric layer;
a matching layer disposed above the piezoelectric layer and comprising one or more grooves connected to the one or more kerfs; and
a third electrode formed in inner surfaces of the one or more grooves and electrically connected to the first electrode,
wherein a width of the groove is formed larger than a width of the kerf such that a separation distance of the third electrode in the elevation direction within the groove is larger than the width of the kerf.

2. The ultrasonic probe according to claim 1, wherein the third electrode is formed by a sputtering method.

3. The ultrasonic probe according to claim 1, further comprising
a fourth electrode formed on one surface of the matching layer provided on a side where the matching layer and the piezoelectric layer are in contact with each other to be electrically connected to the first electrode.

4. The ultrasonic probe according to claim 3, wherein the third electrode and the fourth electrode are electrically connected to each other.

5. The ultrasonic probe according to claim 3, wherein the third electrode and the fourth electrode are formed at the same time by a sputtering method.

6. The ultrasonic probe according to claim 1, further comprising
a circuit layer disposed below the piezoelectric layer.

7. The ultrasonic probe according to claim 6, wherein the circuit layer is made of a flexible printed circuit board (FPCB) to be electrically connected to the second electrode.

8. The ultrasonic probe according to claim 6, wherein the kerfs formed on the piezoelectric layer are continuously formed on a reflective layer.

9. The ultrasonic probe according to claim 8, wherein the kerf is formed on the reflective layer at the same position as the piezoelectric layer.

10. The ultrasonic probe according to claim 1, wherein a depth of the one or more grooves is formed smaller than a thickness of the matching layer.

11. The ultrasonic probe according to claim 1, wherein the matching layer is a first matching layer, and the ultrasonic probe further comprises a second matching layer disposed above the first matching layer.

12. The ultrasonic probe according to claim 11, wherein a depth of the one or more grooves is formed larger than a thickness of the first matching layer and smaller than the combined thickness of the first matching layer and the second matching layer.

13. The ultrasonic probe according to claim 1, wherein the first electrode is a ground electrode and the second electrode is a signal electrode.

14. The ultrasonic probe according to claim 1, wherein the matching layer is made of a non-conductive material.

15. An ultrasonic probe comprising:
a piezoelectric layer comprising one or more kerfs such that piezoelectric elements are provided in a plurality of rows along an elevation direction;
a first electrode formed on an upper side of the piezoelectric layer;
a second electrode formed on a lower side of the piezoelectric layer;
a matching layer disposed above the piezoelectric layer and comprising one or more grooves connected to the one or more kerfs; and
a third electrode made of a conductive material filled in the one or more grooves and electrically connected to the first electrode,
wherein a width of the groove is formed larger than a width of the kerf such that a separation distance of the third electrode in the elevation direction within the groove is larger than the width of the kerf.

16. The ultrasonic probe according to claim 15, further comprising
a fourth electrode formed on one surface of the matching layer provided on a side where the matching layer and the piezoelectric layer are in contact with each other to be electrically connected to the first electrode,
wherein the fourth electrode is electrically connected to the third electrode.

17. A method of manufacturing an ultrasonic probe comprising:
forming one or more grooves on a matching layer along an elevation direction;
forming electrodes in inner surfaces of the one or more grooves and in a lower surface of the matching layer;
adhering the piezoelectric layer to the lower surface of the matching layer; and
forming one or more kerfs in the piezoelectric layer with widths smaller than or equal to widths of the one or more grooves to correspond to positions of the one or more grooves so that the piezoelectric layer is divided into a plurality of rows along the elevation direction,
wherein a width of the groove is formed larger than a width of the kerf such that a separation distance of the electrode in the elevation direction within the groove is larger than the width of the kerf.

18. The method according to claim 17, wherein the electrode formed on the matching layer is electrically connected to a ground electrode of the piezoelectric layer.

* * * * *